United States Patent [19]

Widmer

[11] Patent Number: Plant 7,269

[45] Date of Patent: Jul. 10, 1990

[54] CHRYSANTHEMUM PLANT NAMED MAROON PRIDE

[75] Inventor: Richard E. Widmer, St. Paul, Minn.

[73] Assignee: Regents of the University of Minnesota, Minneapolis, Minn.

[21] Appl. No.: 274,010

[22] Filed: Nov. 21, 1988

[51] Int. Cl.[5] ..... A01H 5/00

[52] U.S. Cl. ..... Plt./82

[58] Field of Search ..... Plt./82

*Primary Examiner*—James R. Feyrer

*Attorney, Agent, or Firm*—Merchant, Gould, Smith, Edell, Welter & Schmidt

[57] ABSTRACT

A new variety of *Dendranthema grandiflora* (*Chrysanthemum morifolium* Ramat.) for the outdoor garden and for spring flowering greenhouse pot plant culture, characterized by flowers which are early opening, rich dark-red in color, slow fading, fully double, flat decorative, and 7.5–9 cm in diameter in an open spray formation. This plant is unique within its color range for earliness, size of bloom and color retention.

2 Drawing Sheets

BACKGROUND INFORMATION

This new cultivar of Chrysanthemum plant originated as seedling number 82-A31-12 resulting from a cross of Ruby Mound and Autumn Fire (unpatented cultivars) made in 1981 at St. Paul, Minn. during the course of breeding efforts in an on-going garden Chrysanthemum breeding project under direction of the inventor, a professor at the University of Minnesota, Department of Horticultural Science and Landscape Architecture.

Minnesota Selection (MN Sel.) 82-A31-12 was discovered as one flowering plant within the progeny of the stated cross in the fall of 1982, in the St. Paul campus field test plots at the University of Minnesota. The early opening of the large (7.5–9 cm) rich, dark red flowers on a high-mounded plant caused the inventor to select this seedling for propagation and testing. The first act of asexual reproduction of MN Sel. 82-A31-12 was accomplished when vegetative cuttings were taken in March-April 1983, in a controlled environment in St. Paul, Minn. Cuttings were from the initial selection plant that had been dug from the field in late October, 1982. Plants so reproduced continued to have the same favorable characteristics on tidy plants with clean, semi-glossy, medium dark green foliage, and the flower color was slow to fade to a light red.

Plants of this Chrysanthemum were field tested at seven locations in Minnesota in 1985, 1986 and 1987, including the Minnesota Landscape Arboretum and the Crookston, Grand Rapids, Lamberton, Morris, Rosemount and Waseca Agricultural Experiment Stations). In addition, this cultivar was trialed in 1985, 1986 and 1987 as a greenhouse grown, spring flowering plant in 3-inch pots. Rooted cuttings were potted March 15 of each year, pinched (stem tip removal) one week later and successfully forced into bloom in both natural (long day) and short day (0800–1600 hours) photoperiods.

Flowering time of this selection in the St. Paul Campus field test plots of the University of Minnesota was earlier than that of all of the other dark reds in the garden Chrysanthemum collection except the cultivar 'Torch Song', and 3 to 4 weeks earlier than 'Minngopher' and 'Minnruby'.

DESCRIPTION OF THE DRAWINGS

This new Chrysanthemum is illustrated by the accompanying photographs.

DESCRIPTION OF THE NEW PLANT

Figure 1:
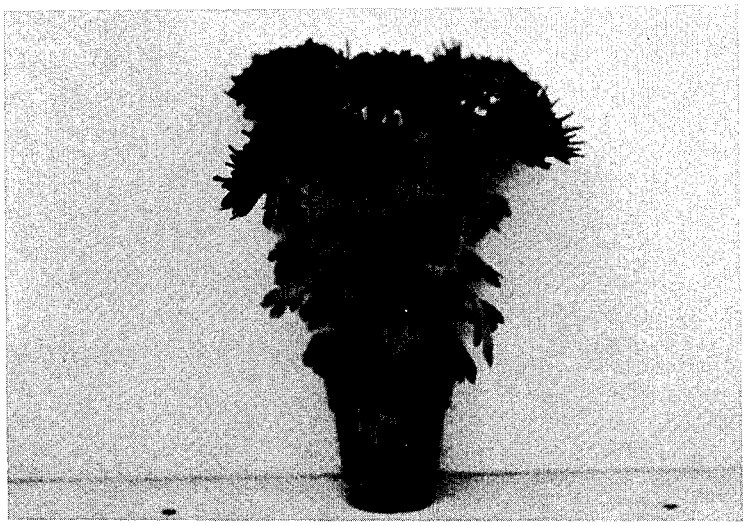
FIG. 1 is a black and white photo of a greenhouse grown flowering plant in a 7.5 cm pot photographed in May, 1988.
Figure 2:
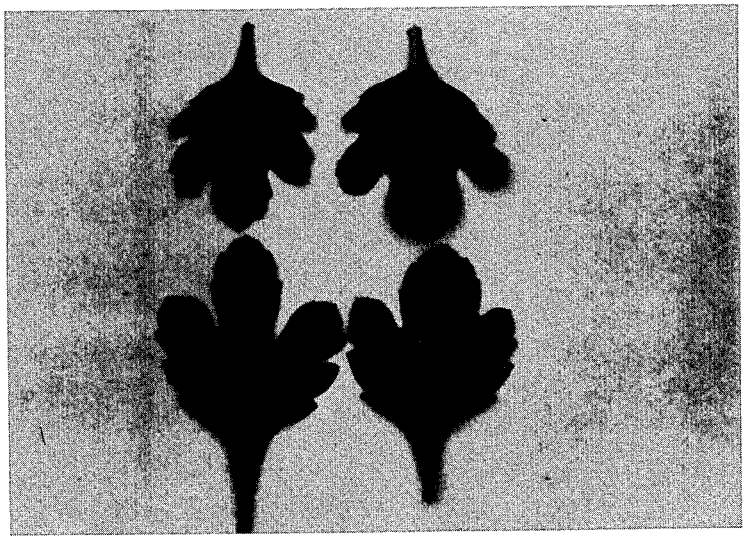
FIG. 2 is a black and white photo showing the under and upper surfaces of leaves from flowering plants of this cultivar.
Figure 3:
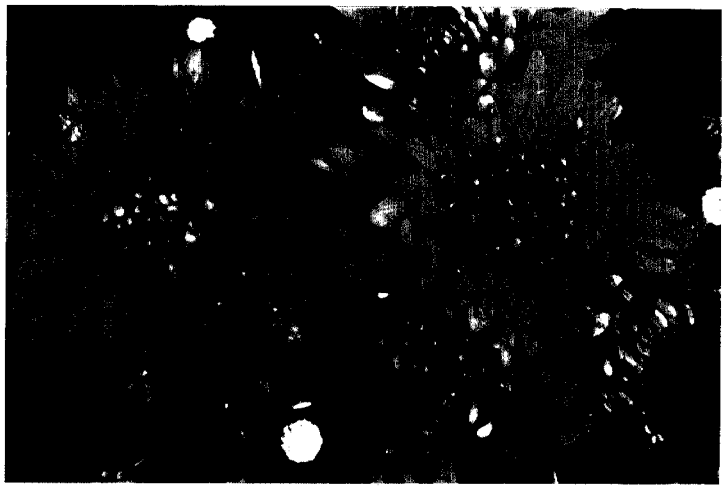
FIG. 3 is a color photograph of a field grown plant in bloom in September, 1989, taken at the trial plots on the St. Paul Campus, University of Minnesota.

The following is a detailed description of the new Chrysanthemum cultivar with color designations according to the R.H.S. Colour Chart published by The Royal Horticultural Society, London, England (Copyright 1938). The observations were made of plants reproduced and grown at the trial plots on the St. Paul Campus, University of Minnesota, St. Paul, Minn.

THE PLANT

Origin: Seedling.

Parentage:

*Seed parent.*—Ruby Mound (unpatented).

*Pollen parent.*—Autumn Fire (unpatented). Cultivar identified as MN. Sel. 82-A31-12.

Classification:

*Botanic.*—*Dendranthema grandiflora* (*Chrysanthemum morifoluim* Ramat.)

*Commercial.*—Greenhouse pot plant and outdoor garden plant.

Form: Perennial herbaceous bush.

Height:

*As a pot plant.*—21 to 28 cm above pot rim.

*As an outdoor garden plant.*—40 to 50 cm.

Growth: Terminal, spreading to form a mound, moderate sturdiness and strength.

Foliage: 5 to 7 leaves per 10 cm of stem.

*Leaf size.*—About 5 cm across and 9 cm long. Shape: Ovate, lobed and deeply incised. Color: Upper side—Spinach Green 960/1. Lower side—spinach Green 960/0. Surface texture: Gladrous, beady. Venation: Pinnately veined. Petioles: About 1.6 cm in length.

THE BUD

Form: Elliptical.
Size:
*Diameter.*—0.7 to 1 cm.
*Depth.*—0.5 cm.
Opening: The bud opens slowly.
Color: When phyllaries first divide, Spinach Green 960/1. When florets begin to unfurl, Ruby Red 827.
Phyllaries: The outside of the receptacle bears many phyllaries as involucral bracts.
Form: Spear shaped and flat.
Color:
*Inside surface.*—Spinach Green 960/1.
*Outside surface.*—Spinach Green 960/1.
*Surface texture.*—Shiny below pubescence.
Peduncle: Length— about 11 to 13 cm.
*Surface texture.*—Minutely pubescent.
*Strength.*—Moderate.
*Color.*—Spinach Green 960/3.

THE FLOWER

Blooming:
*Capability.*—This plant can be flowered the year round with photoperiod and temperature control.
*Responses.*—5-6 weeks. Natural flowering season: August 24 to October 15.
*Blooms.*—Flower type: Decorative with occasional tubercular florets. Diameter: 7.5-9 cm. Depth: 2.5 cm.
Shape.—Flat when bloom first opens, becoming more hemispherical as the bloom matures.
*Borne.*—Singly, as a head of many florets on a receptacle, in a spray formation.
Florets: Numerous.
*Form.*—Exobtuse apex, linear.
*Arrangement.*—Decorative.
*Texture.*—Medium.
*Appearance.*—Very little shine.
*Discoloration.*—Very little fade.
Color: May (Indoor), September (outdoor).
*Outer florets.*—

| | | |
|---|---|---|
| Upper side | Cardinal Red 822 | Cardinal Red 822/1 |
| Reverse | Jasper Red 018/1 | Jasper Red 018/1 |

*Inside florets.*—

| | | |
|---|---|---|
| Upper side | Cardinal Red 822 | Cardinal Red 822 |
| Reverse | Jasper Red 018/01 | Chrysanthemum Crimson 824 |

General color tonality of bloom: Cardinal Red 822/1 at a distance of 6 feet. (May). Currant Red 821/1 at a distance of 6 feet. (Sept).
Effect of weather: Flower is not affected by hot or wet weather.
Persistance: Florets hang on and dry.
Fragrance: Typical Chrysanthemum.
Lasting quality: On plant— 3 weeks to a month; a good cut flower.

REPRODUCTIVE ORGANS

Stamens: None.
Pistils:
*Number.*—One per each ray floret.
*Styles.*—About 0.15 cm long.
*Stigmas.*—Color— Sulfur yellow/3.
Ovaries: Inferior bicarpellate.

I claim:

1. A new and distinct *Dendranthema grandiflora* cultivar substantially as shown and described herein, and particularly characterized by blooms which are reliably early, 7.5-9.0 cm in diameter, dark red, slow-fading double florets of decorative form, presented in open spray formation on uniform, medium high, mounded plants of moderate sturdiness and strength, with small to medium sized foliage.

* * * * *